(12) United States Patent
Terashima et al.

(10) Patent No.: US 6,869,512 B2
(45) Date of Patent: Mar. 22, 2005

(54) DEVICE FOR MEASURING IONIC ACTIVITIES

(75) Inventors: Masaaki Terashima, Saitama (JP); Osamu Seshimoto, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 391 days.

(21) Appl. No.: 10/006,169

(22) Filed: Dec. 6, 2001

(65) Prior Publication Data

US 2002/0066670 A1 Jun. 6, 2002

(30) Foreign Application Priority Data

Dec. 6, 2000 (JP) ......................................... 2000-371634

(51) Int. Cl.[7] ............................................. G01N 27/333
(52) U.S. Cl. ...................................... 204/416; 204/418
(58) Field of Search ................................ 204/416–419, 204/412, 409–411; 422/82.03

(56) References Cited

U.S. PATENT DOCUMENTS

| 4,053,381 A | 10/1977 | Hambien et al. ............ 204/416 |
| 4,171,246 A | 10/1979 | Hambien et al. ......... 205/778.5 |
| 4,219,968 A | 9/1980 | Sakai et al. ..................... 49/40 |
| 4,302,313 A | 11/1981 | Columbus ................ 204/195 R |
| 4,510,035 A | 4/1985 | Seshimoto ................... 204/411 |
| 4,571,293 A | 2/1986 | Seshimoto et al. .......... 204/418 |
| 4,789,435 A | 12/1988 | Seshimoto et al. .......... 205/789 |
| 4,842,712 A | 6/1989 | Seshimoto et al. .......... 204/416 |
| 5,626,740 A | 5/1997 | Seto et al. ................... 205/789 |

FOREIGN PATENT DOCUMENTS

EP 0121 936 10/1984

Primary Examiner—Alex Noguerola
(74) Attorney, Agent, or Firm—Reed Smith LLP

(57) ABSTRACT

A device for measuring ionic activity is composed of:

a block of insulating material having a hollow space therein, a solution-receiving surface area in which a pair of openings for receiving a sample solution and a reference solution separately are provided, a plurality of solution-supplying surface areas in each of which a pair of openings for supplying outside the sample solution and the reference solution separately are provided;

a bridge member fixed on the solution-receiving surface area;

a guide member placed in the hollow space which assists to transmit separately the sample solution and the reference member in the hollow space; and two or more ion selective electrodes each of which is placed on each solution-supplying surface area.

8 Claims, 10 Drawing Sheets

(1)

(2)

(3)

(1)

(2)

(1)

(2)

DEVICE FOR MEASURING IONIC ACTIVITIES

CROSS-REFERENCES TO RELATED APPLICATIONS

This application claims priority of Japanese Application No. 2000-371634 filed Dec. 6, 2000, the complete disclosure of which is hereby incorporated by reference.

FIELD OF THE INVENTION

This invention relates to a device for measuring ionic activities of various ionic components contained in a sample solution, which is favorably employable for simultaneous analysis of ionic components in liquid samples such as a whole blood sample, a serum sample, and a urine sample.

BACKGROUND OF THE INVENTION

An ionic activity-measuring device utilizing an ion selective electrode is widely employed for analyzing ionic components in a liquid sample such as a whole blood sample or a serum sample.

U.S. Pat. No. 4,571,293 (which corresponds to EP 0 160 997 B1) discloses an ionic activity-measuring device using an ion selective electrode which is illustrated in FIG. 1 of the drawings attached to this specification.

In FIG. 1, the ionic activity-measuring device comprises a non-electroconductive support 11, a pair of electrodes each of which comprises a silver metal layer 12a, 12b and a silver halide layer 13a, 13b, a common electrolytic material layer 14, a common ion selective membrane 15, and a common non-electroconductive cover sheet 16 having a pair of openings 17a, 17b for receiving and keeping a sample solution and a reference solution, respectively, each opening being placed over each electrode unit, and having thereon an a bridge member 18 for electrically bridging the sample solution received in one opening 17a and the reference solution received in another opening 17b. Each silver metal layer 12a, 12b has an exposed surface 10a, 10b, respectively. By placing probes of a potentiometer 19 on these exposed silver metal surfaces 10a, 10b, the produced electric potential difference can be measured.

The ion selective electrode can measure an ionic activity of an ionic component such as $H^+$, $Li^+$, $Na^+$, $K^+$, $Mg^{2+}$, $Ca^{2+}$, $Cl^-$, $HCO_3^-$, or $CO_3^{2-}$, by employing an appropriate ion selective membrane.

U.S. Pat. No. 4,789,435 describes an ion selective electrode assembly comprising plural ion selective electrodes for analyzing plural ionic components such as $Na^+$, $K^+$, and $Cl^-$, simultaneously. In the assembly, one of plural ion selective electrodes has an ion selective membrane differing from that of other ion selective electrode in chemical composition.

SUMMARY OF THE INVENTION

It is an object of the present invention to provide a device for measuring simultaneously ionic activities of plural ionic components contained in an aqueous sample.

The invention resides in a device for measuring ionic activity which comprises:

a block of insulating material having a hollow space therein, a solution-receiving surface area in which a pair of openings for receiving a sample solution and a reference solution separately are provided, said openings connecting with the hollow space, a plurality of solution-supplying surface areas in each of which a pair of openings for supplying outside the sample solution and the reference solution separately are provided, said openings connecting with the hollow space;

a bridge member provided on the solution-receiving surface area for electrically bridging the sample solution received in one opening and the reference solution received in another opening;

a guide member placed in the hollow space which assists to transmit separately the sample solution received in the opening in the solution-receiving surface area to the openings on the solution-supplying surface areas for the supplying outside the sample solution and the reference solution received in the opening in the solution-receiving surface area to the openings on the solution-supplying surface areas for the supplying outside the reference solution;

and a plurality of ion selective electrodes having an ion selective membrane thereon each of which is placed on the solution-supplying surface area under such condition that the ion selective membrane is brought into contact with the sample solution and the reference solution separately.

Preferred devices according to the invention are as follows.

(1) The device wherein the guide member is a partition which is placed in the hollow space to guide separately the sample solution and the reference solution.

(2) The device wherein the guide member comprises a pair of porous liquid-transmitting materials placed in the hollow space, one of which transmits the sample solution and another of which transmits the reference solution.

(3) The device wherein the block is in the form of a rectangular parallelepiped having a upper surface on which the solution-receiving surface area is arranged, and other surfaces including a bottom surface and side surfaces on at least two of which the solution-supplying surface area is arranged.

(4) The device wherein the block is in the form of a horizontally extended rectangular parallelepiped having a upper surface on which the solution-receiving surface area is arranged, a bottom surface, and side surfaces, the plurality of the solution-supplying surface areas are arranged on at least one of these surfaces.

(5) The device wherein the block is in the form of a vertically extended rectangular parallelepiped having a upper surface on which the solution-receiving surface area is arranged, and other surfaces including a bottom surface and side surfaces on at least two of which the solution-supplying surface area is arranged.

DETAILED DESCRIPTION OF THE INVENTION

The ionic activity-measuring device of the present invention is further described by referring to the fig.

Figure 2:
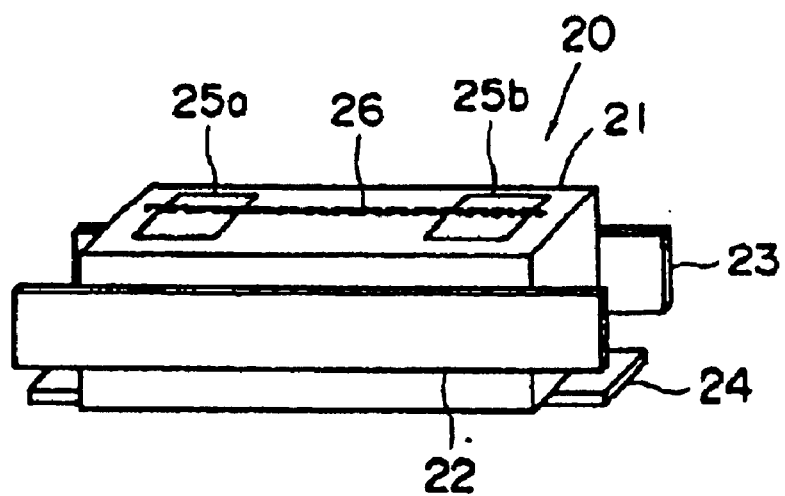
FIG. 2 is a schematic view of a representative structure of the ionic activity-measuring device according to the invention.
Figure 3:
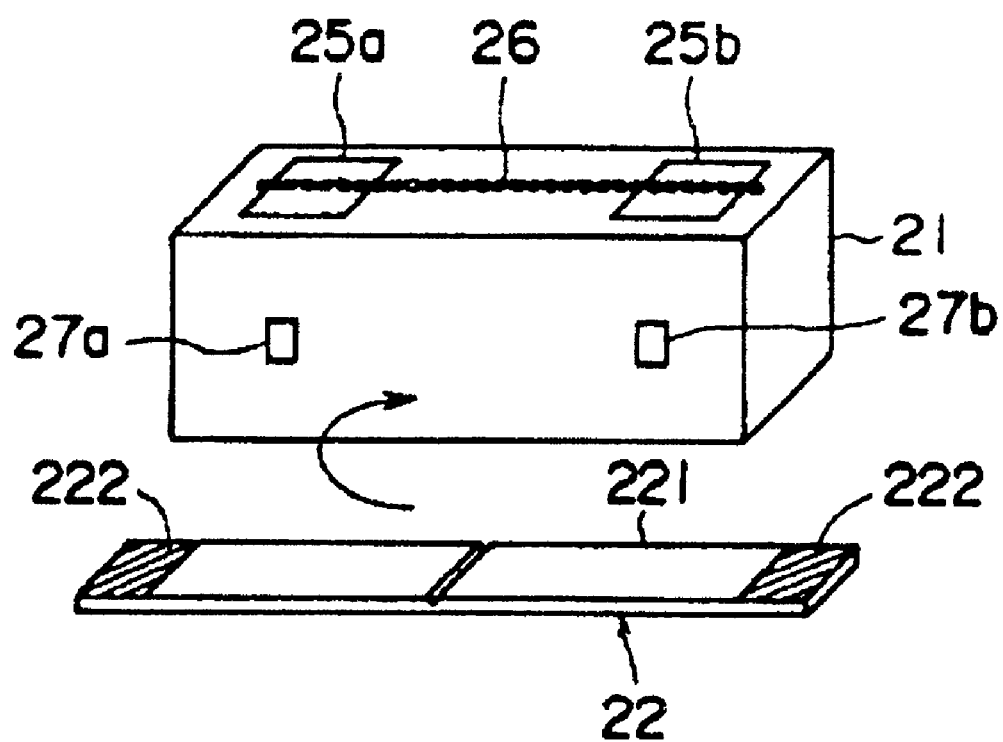
FIG. 3 is a schematic view of the device of FIG. 2 in a disassembled form.

FIG. 2 is a schematic view of a typical structure of the ionic activity-measuring device according to the invention, and FIG. 3 is a schematic view of the device of FIG. 2 in a disassembled form.

In FIG. 2 and FIG. 3, an ionic activity-measuring device 20 is composed of a block 21 of rectangular parallelepiped which has a hollow space in its inside, and three sets of ion selective electrode sheets 22, 23, 24 which are attached to the side surfaces and bottom surface of the block 21. On the upper surface of the block 21, an opening 25*a* for receiving a spotted sample solution and an opening 25*b* for receiving a spotted reference solution are provided, and a bridge member (fiber bridge) 26 for electrically connecting the received sample solution with the received reference solution is fixed. On each of the side surfaces and bottom surface of the block 21, a pair of openings 27*a*, 27*b* for supplying separately the received sample solution and the received reference solution onto the ion selective electrode sheet.

The block 21 is made of water-impermeable, electrically insulating material such as polystyrene. The fiber bridge 26 is made from polyethylene terephthalate thrown fibers.

Figure 1:
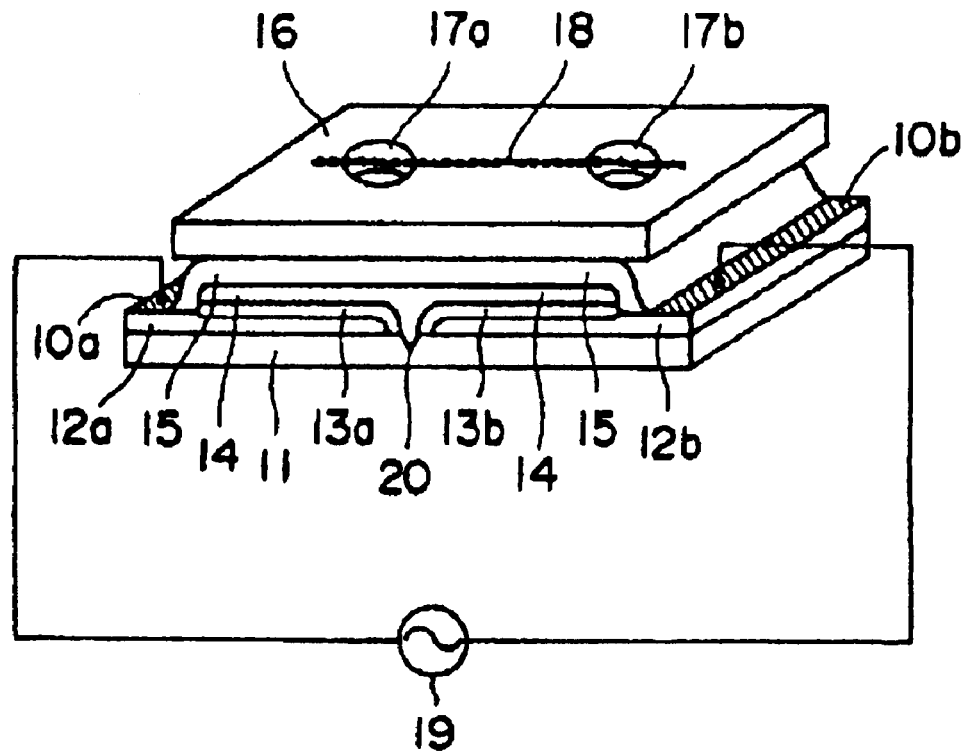
FIG. 1 is a schematic view of a representative structure of a conventional ionic activity-measuring device.

Each of the ion selective electrode sheets 22, 23, 24 is composed of an non-electroconductive support, a silver layer, a silver chloride layer, an electrolytic material layer and an ion selective membrane, as shown in FIG. 1. The ion selective electrode sheets 22, 23, 24 preferably have ion selective membranes different from each other, so that ionic activities of plural ionic components are measured in one device. The ion selective electrode sheet 22 is fixed to the surface of the block 21 under such condition that the uppermost ion selective membrane 221 faces the openings 27*a*, 27*b* and the electrode terminals 222 are extended from the edges of the block 21.

Figure 4:
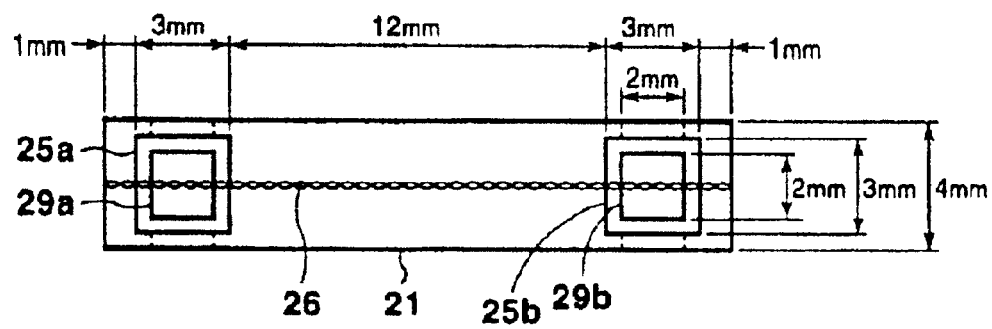
FIG. 4 illustrates an inner structure of the block of the device of FIG. 2.
Figure 4:
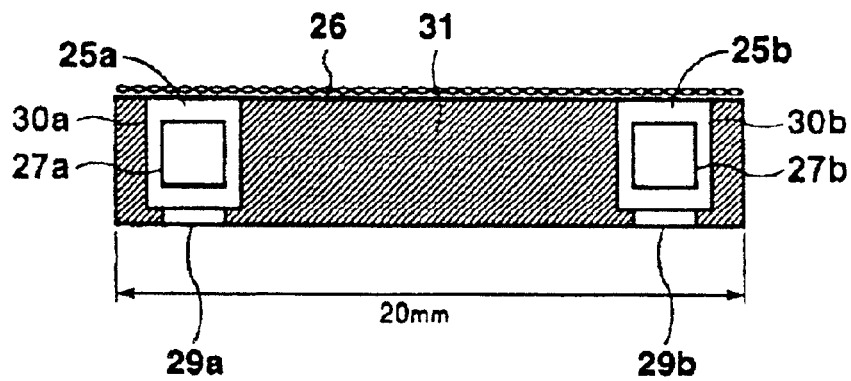
Figure 4:
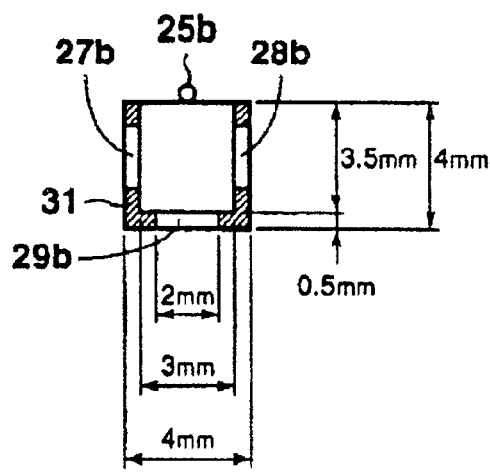

In FIG. 4, (1) indicates a upper surface of the hollow block 21, (2) is a front view, and (3) is a side view. In FIG. 4, the inner hollow space of the block 21 has a pair of solution reservoirs 30*a*, 30*b* which are separated by a partition 31 to supply the sample solution received in the opening 25*a* and the reference solution received in the opening 25*b* separately to the solution-supplying openings 27*a*, 28*a*, 29*a*, and the solution-supplying openings 27*b*, 28*b*, 29*b*, respectively.

The block 21 typically has a dimension of 4 mm×20 mm×4 mm (height), as illustrated in FIG. 4. Each of the solution-receiving openings 25*a*, 25*b* has a dimension of 3 mm×3 mm. Each of the solution-supplying openings 27*a*, 27*b* has a dimension of 2 mm×2 mm, while each of the solution reservoirs 30*a*, 30*b* has a dimension of 3 mm×3 mm×3.5 mm.

Figure 5:
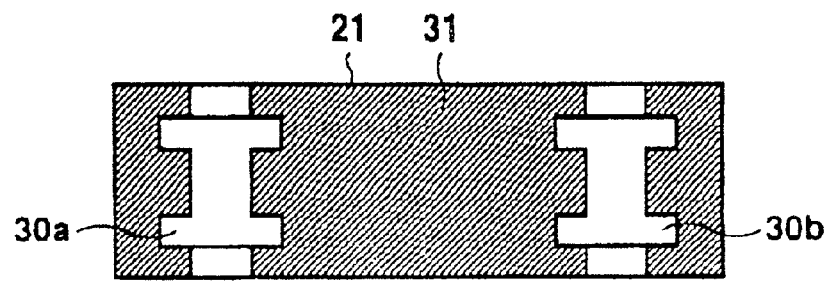
FIG. 5 is a horizontal section of an inner structure of a block of different structure.
Figure 6:
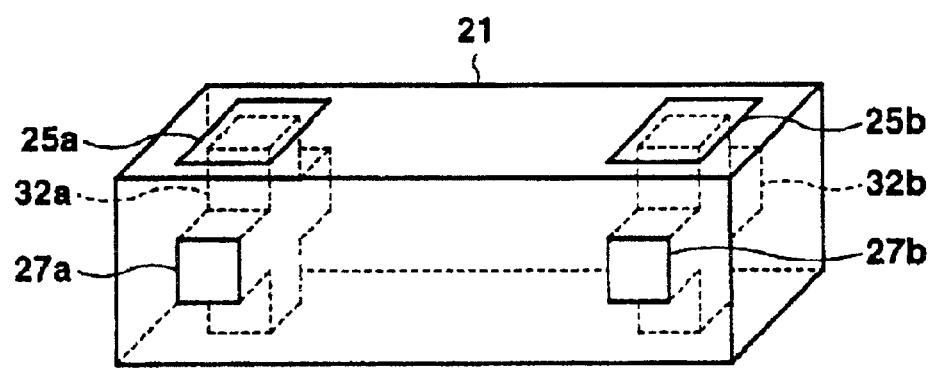
FIG. 6 is a schematic view of an inner structure of a block of different structure.

The structure of the block 21 is not limited to that illustrated in FIG. 4. For instance, the partition 31 is a plate arranged in the inner hollow space at the center position. Otherwise, a part of the partition 31' extends to both side portions into the reservoirs 30*a*, 30*b* so as to reduce the volume of the reservoir, as is shown in FIG. 5. Alternatively, a pair of porous materials 32*a*, 32*b* are placed independently in both reservoirs to transmit the sample solution and the reference solution, separately, as is shown in FIG. 6.

Figure 7:
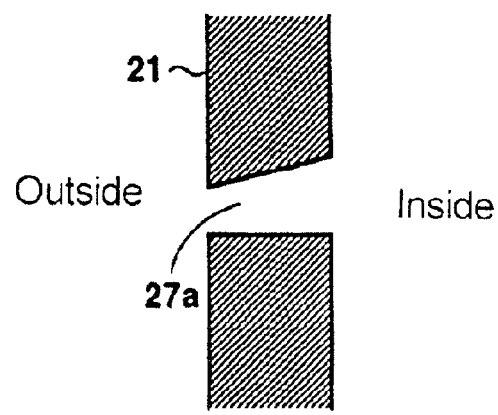
FIG. 7 is a partly enlarged view of a vertical section of a solution-supplying opening.

Each of the solution-supplying openings 27*a*, 27*b*, 28*a*, 28*b* can have a slanting ceiling from the inside to the outside, as is shown in FIG. 7, so that air bubbles are not produced in the opening.

The upper surface of the block 21 can have a groove for protecting the fiber bridge 26 and further for reducing a required volume of the solutions. The fiber bridge 26 can be placed and fixed in the groove.

Figure 8:
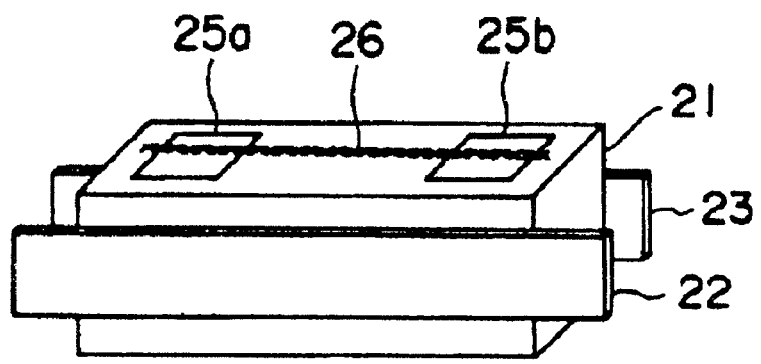
FIG. 8 is a schematic view of an ionic activity-measuring device of the invention having a different structure.
Figure 8:
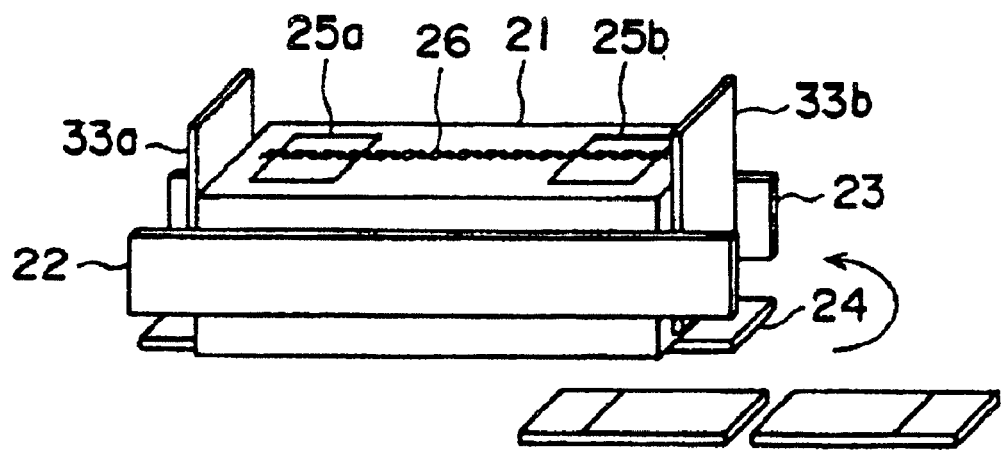

The ion activity-measuring device of the invention is not limited to the above-mentioned structure having three sets of the ion selective electrode sheets. For instance, only two sets of the ion selective electrode sheets 22, 23 are attached to the side surfaces, as is illustrated in FIG. 8-(1). Otherwise, four sets of ion selective electrode sheets 22, 23, 24, 33*a* (in combination with 34*b*) are attached to the side surfaces and the bottom surface, as is illustrated in FIG. 8-(2).

Figure 9:
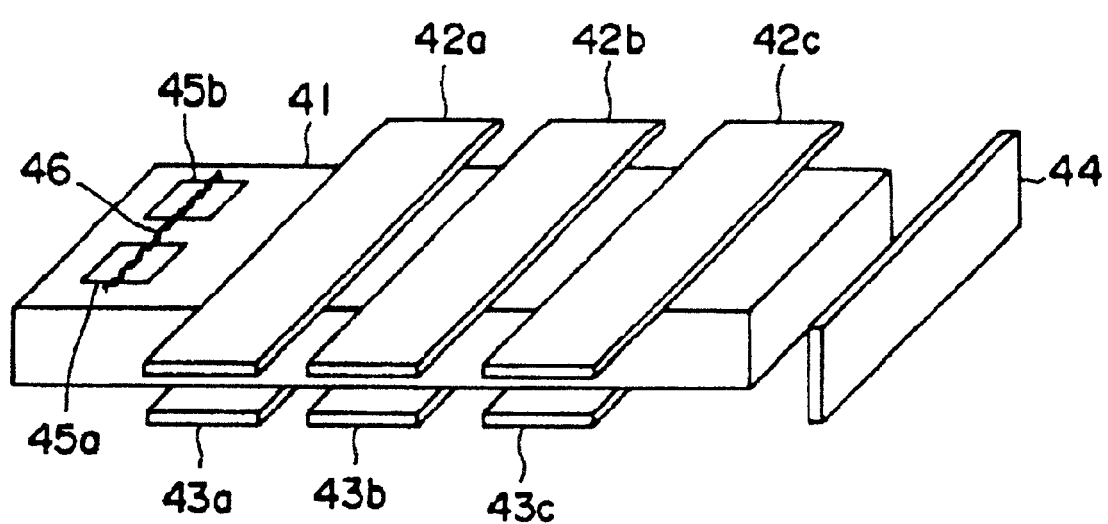
FIG. 9 is a schematic view of an ionic activity-measuring device of the invention having a different structure.

Alternatively, seven sets of ion selective electrode sheets 42*a*, 42*b*, 42*c*, 43*a*, 43*b*, 43*c*, 44 attached to the block 41 on the upper surface, bottom surface, the side surfaces, as is illustrated FIG. 9. On each of the upper surface and the bottom surface, the electrode sheets 42*a* to 42*c*, and 43*a* to 43*c* are placed in parallel. On the upper surface of the block 42 are arranged the solution-receiving openings 45*a*, 45*b* and the fiber bridge 46. The electrode sheets attached to the upper surface and bottom surface can be two sets or four sets in place of the above-mentioned three sets. The electrode sheets may be not attached to the side surfaces, or may be attached only one of the upper surface and bottom surface.

Figure 10:
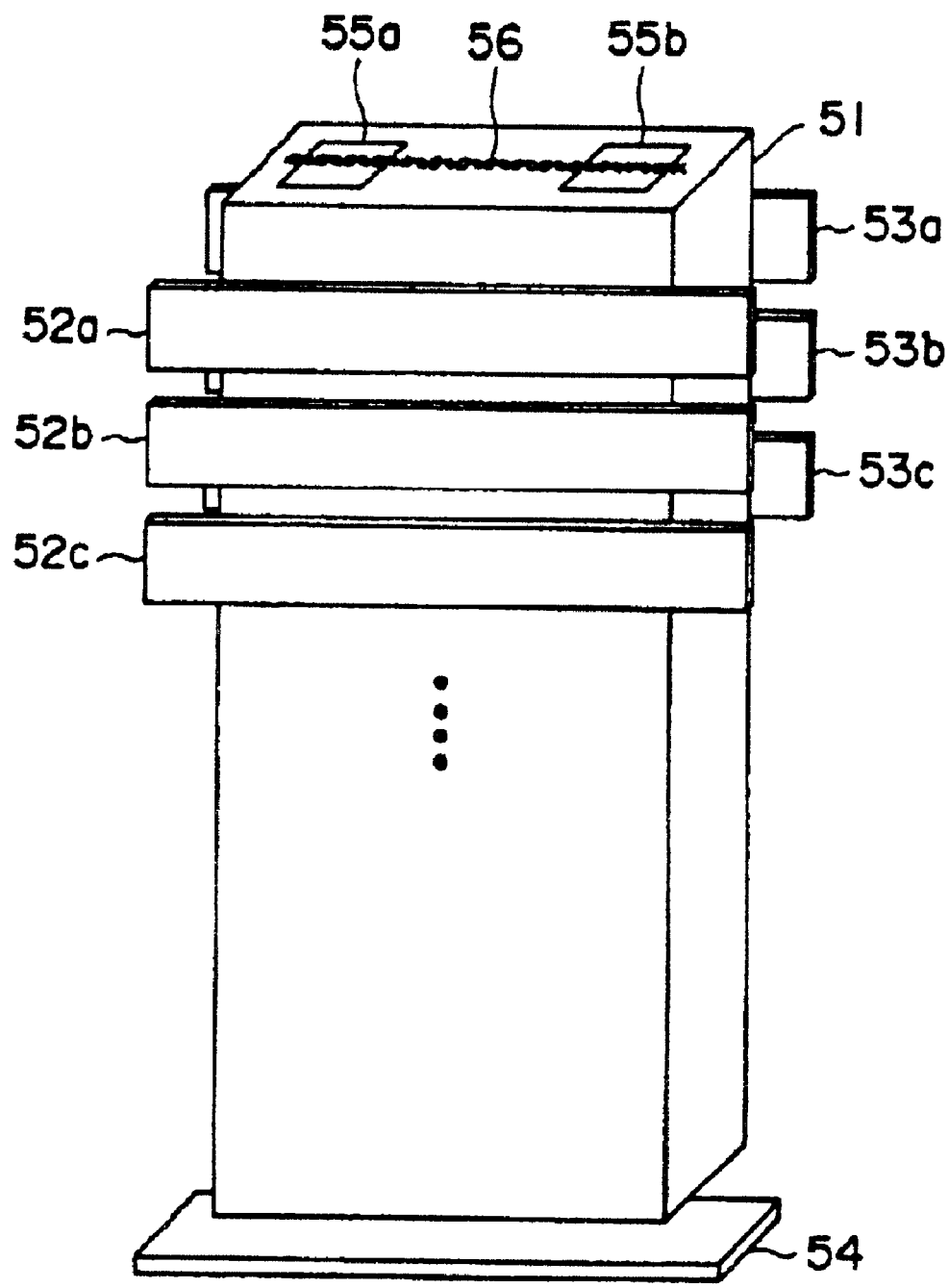
FIG. 10 is a schematic view of an ionic activity-measuring device of the invention having a different structure.

The ionic activity-measuring device can be composed of a vertically extended block 51 and several sets of ion selective electrode sheets 52*a*, 52*b*, 52*c*, - - -, 53*a*, 53*b*, 53*c*, - - -, 54, which are attached to the side surfaces and the bottom surface, as is illustrated in FIG. 10. On the side surfaces, the electrode sheets are arranged in parallel. On the upper surface of the block 51 are provided the solution-receiving openings 55*a*, 55*b* and the fiber bridge 56. The ion selective electrode sheets attached to the side surface can be two or three sheets. The electrode sheet may not attached to the bottom surface, and may be attached to one side surface only.

Figure 11:
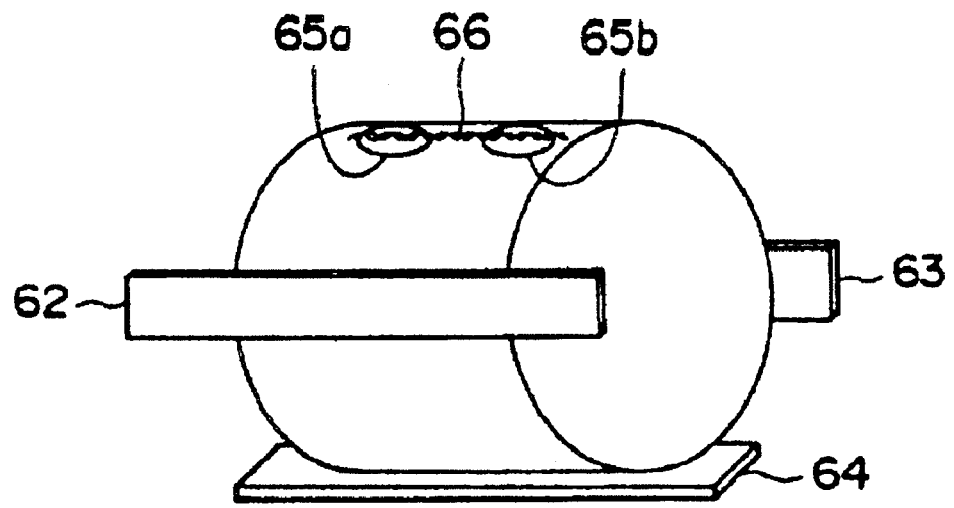
FIG. 11 is a schematic view of an ionic activity-measuring device of the invention having a different structure.

The ionic activity-measuring device can be composed of a block 61 in a drum form and three sets of ion selective electrode sheets 62, 63, 64 which are attached to the side surfaces and the bottom surface, as is illustrated in FIG. 11. On the upper surface of the block 61, two solution-receiving openings 65*a*, 65*b* and one fiber bridge 66 are place. The ion selective electrode sheets attached to the side surface and the bottom surface can be two, four or more sheets.

Figure 12:
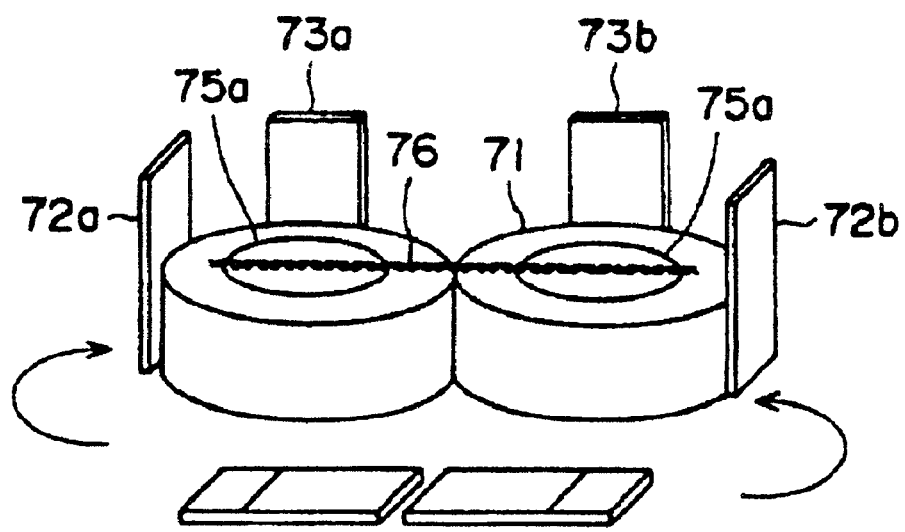
FIG. 12 is a schematic view of an ionic activity-measuring device of the invention having a different structure.

The ionic activity-measuring device can be composed of a block 71 composed two drums united to each other and two sets of ion selective electrode sheets 72a, 72b, 73a, 73b, as illustrated in FIG. 12. In FIG. 12, the electrode sheet is composed of a pair of single electrode 72a (73a) and single electrode 72b (73b), which are separated from each other. On the upper surface of the block 71 are provided solution-receiving openings 75a, 75b and a fiber bridge 76. Three or more electrode sheets can be attached to the side surface, and an ion selective electrode sheet can be attached to the bottom surface.

The drum structure can be replaced with other structures such as polygonal pillar such as pentagonal pillar, hexagonal pillar, and octagonal pillar. On the side surfaces and/or bottom surfaces can be attached ion selective electrode sheets.

The preparation of the ionic activity-measuring device of the invention is described by referring to the device of FIG. 2.

First, plastic material such as polyolefin (e.g., polystyrene) is molded to produce a block of FIG. 3.

Independently, three sets of ion selective electrode sheets each of which has a different ion selective membrane are prepared in one of known manners describe, for instance, in U.S. Pat. Nos. 4,053,381, 4,171,246, 4,219,968, and Research Disclosure, No. 16113 (1977, September). A representative ion selective electrode sheet is illustrated in FIG. 3.

The three sets of ion selective electrode sheets are attached to the side surfaces and the bottom surface of the block using a double adhesive-coated tape. On the upper surface, a fiber bridge made of a polyethylene terephthalate thrown fiber is placed to connect the solution-receiving openings and fixed to the surface using-appropriate adhesive.

Figure 13:
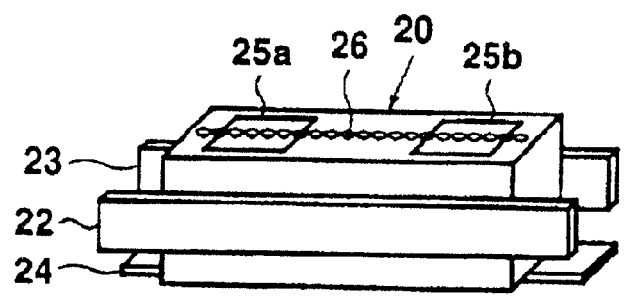
FIG. 13 is a schematic view of a frame for encasing the ionic activity-measuring device of the invention.
Figure 13:
Figure 13:
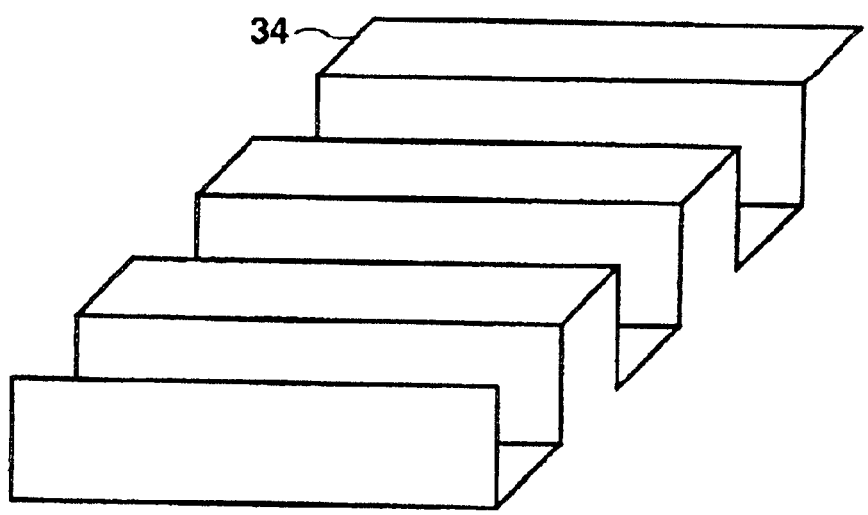
Figure 13:
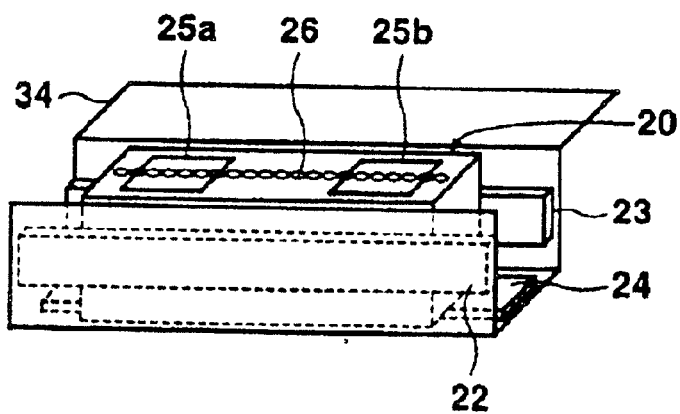
Figure 14:
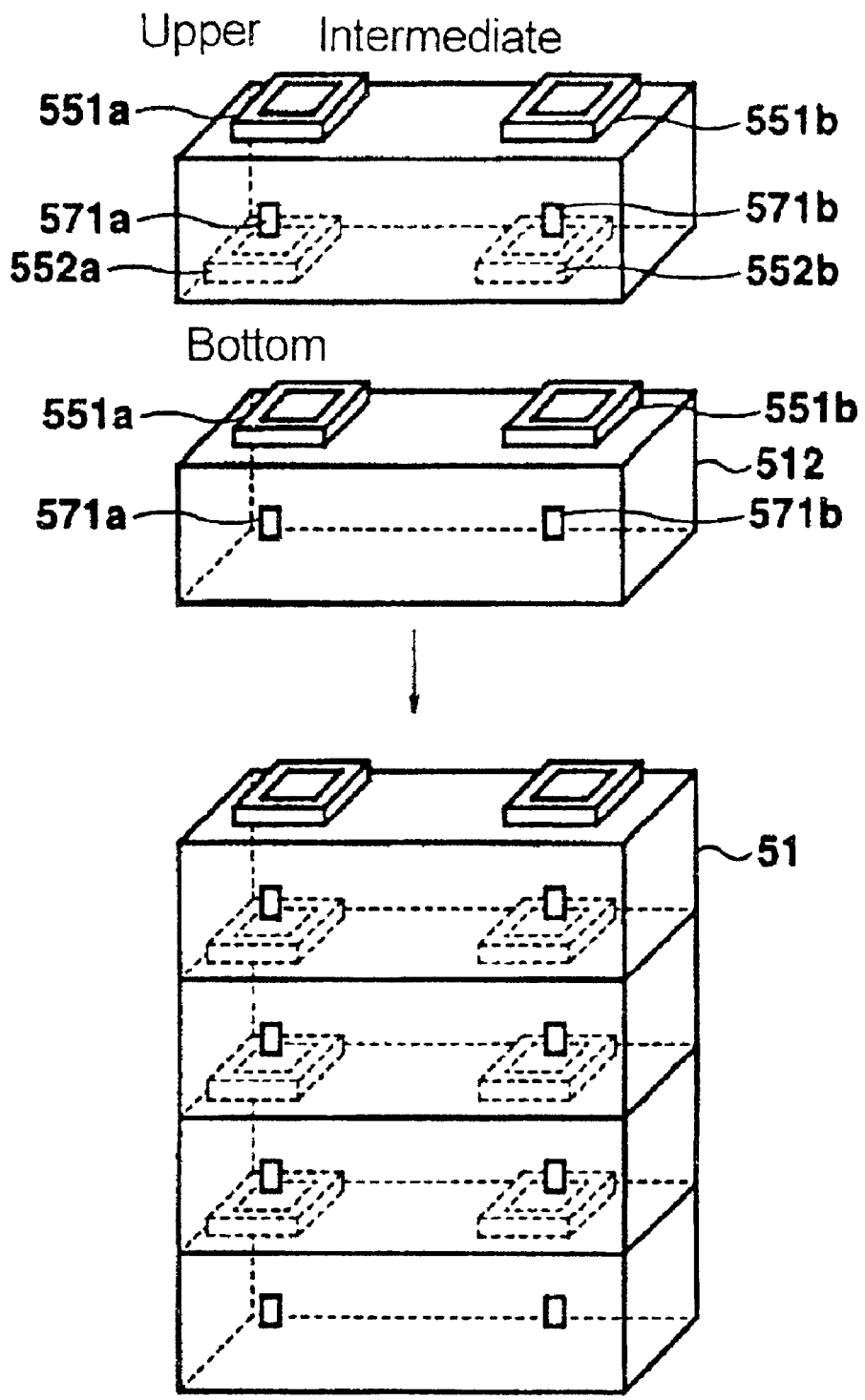
FIG. 14 is a schematic view illustrating manufacture of the block of the device of FIG. 10.

The ionic activity-measuring devices can be manufactured in a mass scale, and a plurality of devices can be conveyed and stored after the devices 20 are encased in a frame 34 made of plastic material, as is shown in FIG. 13-(1). For the use of the encased device, each device is separated together with its casing, and placed in a potentiometer for the desired measurement.

For manufacturing the vertically extended ionic activity-measuring device of FIG. 10, two block units 511, 512 (551a, 551b, 552a, 552b: solution-receiving opening, 571a, 571b: solution-supplying opening) are produced in several numbers and jointed together in the vertical direction to give the desired vertically extended block 51.

What is claimed is:

1. A device for measuring ionic activity which comprises:
    a block of insulating material having a hollow space therein, a solution-receiving surface area in which a pair of openings for receiving a sample solution and a reference solution separately are provided, said openings connecting with the hollow space, a plurality of solution-supplying surface areas in each of which are provided a pair of openings for supplying to outside the device the sample solution and the reference solution separately, said openings connecting with the hollow space, said block being in the form of a rectangular parallelepiped having an upper surface on which the solution-receiving surface area is arranged, and other surfaces including a bottom surface and side surfaces on at least two of which solution-supplying surface areas are arranged;
    a bridge member provided on the solution-receiving surface area for electrically bridging the sample solution received in one opening and the reference solution received in another opening;
    a guide member placed in the hollow space which assists to transmit separately the sample solution received in the opening in the solution-receiving surface area to the openings on the solution-supplying surface areas for supplying to outside the device the sample solution and the reference solution received in the opening in the solution-receiving surface area to the openings on the solution-supplying surface areas for supplying to outside the device the reference solution; and
    a plurality of ion selective electrodes each having an ion selective membrane thereon each of which is placed on a different solution-supplying surface area under such condition that the ion selective membrane is brought into contact with the sample solution and the reference solution separately.

2. The device of claim 1, wherein the guide member is a partition which is placed in the hollow space to guide separately the sample solution and the reference solution.

3. The device of claim 1, wherein the guide member comprises a pair of porous liquid-transmitting materials placed in the hollow space, one of which transmits the sample solution and another of which transmits the reference solution.

4. The device of claim 1, wherein the block is in the form of a horizontally extended rectangular parallelepiped having a upper surface on which the solution-receiving surface area is arranged, a bottom surface, and side surfaces, the plurality of the solution-supplying surface areas are arranged on at least one of these surfaces.

5. A device for measuring ionic activity which comprises:
    a block of insulating material having a hollow space therein, a solution-receiving surface area in which a pair of openings for receiving a sample solution and a reference solution separately are provided, said openings connecting with the hollow space, a plurality of solution-supplying surface areas in each of which are provided a pair of openings for supplying to outside the device the sample solution and the reference solution separately, said openings connecting with the hollow space, the block being in the form of a vertically extended rectangular parallelepiped having an upper surface on which the solution-receiving surface area is arranged, and other surfaces including a bottom surface and side surfaces on at least two of which solution-supplying surface areas are arranged;
    a bridge member provided on the solution-receiving surface area for electrically bridging the sample solution received in one opening and the reference solution received in another opening;
    a guide member placed in the hollow space which assists to transmit separately the sample solution received in the opening in the solution-receiving surface area to the openings on the solution-supplying surface areas for supplying to outside the device the sample solution and the reference solution received in the opening in the solution-receiving surface area to the openings on the solution-supplying surface areas for supplying to outside the device the reference solution; and
    a plurality of ion selective electrodes each having an ion selective membrane thereon each of which is placed on a different solution-supplying surface area under such condition that the ion selective membrane is brought into contact with the sample solution and the reference solution separately.

6. The device of claim 5, wherein the guide member is a partition which is placed in the hollow space to guide separately the sample solution and the reference solution.

7. The device of claim 5, wherein the guide member comprises a pair of porous liquid-transmitting materials placed in the hollow space, one of which transmits the sample solution and another of which transmits the reference solution.

8. The device of claim 5, wherein the block is in the form of a horizontally extended rectangular parallelepiped having a upper surface on which the solution-receiving surface area is arranged, a bottom surface, and side surfaces, the plurality of the solution-supplying surface areas are arranged on at least one of these surfaces.

* * * * *